(12) United States Patent
Hsu et al.

(10) Patent No.: US 9,034,636 B2
(45) Date of Patent: May 19, 2015

(54) MICROFLUIDIC HANGING DROP CHIP (71) Applicants: Chia-Hsien Hsu, Miaoli County (TW); Chih-Chen Chen, Miaoli County (TW)

(72) Inventors: Chia-Hsien Hsu, Miaoli County (TW); Chih-Chen Chen, Miaoli County (TW)

(73) Assignees: NATIONAL HEALTH RESEACH INSTITUTES, Miaoli County (TW); NATIONAL TSING HUA UNIVERSITY, Hsinchu (TW)

( * ) Notice: Subject to any disclaimer, the term of this patent is extended or adjusted under 35 U.S.C. 154(b) by 108 days.

(21) Appl. No.: 13/627,213

(22) Filed: Sep. 26, 2012

(65) Prior Publication Data
US 2013/0084634 A1 Apr. 4, 2013

Related U.S. Application Data (60) Provisional application No. 61/541,231, filed on Sep. 30, 2011.

(51) Int. Cl.
C12M 1/00 (2006.01)
C12M 3/06 (2006.01)
C12M 1/12 (2006.01)

(52) U.S. Cl.
CPC ............... *C12M 21/00* (2013.01); *C12M 23/16* (2013.01); *C12M 25/01* (2013.01)

(58) Field of Classification Search
CPC ...... C12M 21/00; C12M 25/01; C12M 23/16; B01L 3/5085; B01L 2300/0858; B01L 2300/0829; G01N 2035/1046; G01N 35/028
USPC .................................... 435/325, 289.1, 286.5
See application file for complete search history.

(56) References Cited

U.S. PATENT DOCUMENTS

| 6,251,343 | B1 | 6/2001 | Dubrow et al. | |
| 2001/0036674 | A1* | 11/2001 | Indermuhle et al. | 436/518 |
| 2007/0052781 | A1 | 3/2007 | Fraden et al. | |
| 2010/0285975 | A1* | 11/2010 | Mathies et al. | 506/7 |
| 2011/0306122 | A1* | 12/2011 | Moritz et al. | 435/325 |
| 2013/0040855 | A1* | 2/2013 | Takayama et al. | 506/10 |

FOREIGN PATENT DOCUMENTS

WO 2010/031194 A1 3/2010

* cited by examiner

*Primary Examiner* — William H Beisner
*Assistant Examiner* — Danielle Henkel
(74) *Attorney, Agent, or Firm* — Hsiu-Ming Saunders; Intellectual Property Connections Inc.

(57) ABSTRACT

A microfluidic hanging drop chip is disclosed. Also disclosed are methods for culturing cells and forming cell aggregates in hanging drops.

20 Claims, 10 Drawing Sheets

| Diameter of opening | Maximum height | Burst pressure |
|---|---|---|
| 500 μm | 4.1 cm | 401.8 N/m² |
| 200 μm | 5.8 cm | 563.5 N/m² |

MICROFLUIDIC HANGING DROP CHIP

REFERENCE TO RELATED APPLICATION

The present application claims the priority to U.S. Provisional Application Ser. No. 61/541,23, filed Sep. 30, 2011, which is herein incorporated by reference in its entirety.

FIELD OF THE INVENTION

The present invention relates generally to a hanging drop platform, and more specifically to a 3D hanging drop device and methods of forming hanging drops.

BACKGROUND OF THE INVENTION

The hanging drop (HD) culture method is widely used for the formation of in vitro 3D aggregation of cells, avoiding the cellular distortion typically seen in the two-dimensional cell culture. The conventional HD technique consists of placing a small drop of medium and cells on a plastic substrate, inverting the substrate, and incubating for the desired length of time. However, the size of the HD is restrained by gravity, and hence only a limited number of cells can be sustained without cumbersome periodic replenishment. Approaches to modified RD method include hollow spheres, 384-well HD culture plates, and microwell structures. In the first two methods, the contents in the HD cannot be exchanged easily. In the microwell system, the substrate must be optimized to support 3D cell growth without cell adhesion

SUMMARY OF THE INVENTION

In one aspect, the invention relates to a microfluidic hanging drop (μHD) chip, which comprises:
(a) a covering portion with a length of L1, a width of W1, and a height or a thickness of T1;
(b) a channel-forming portion with a length of L2, a width of W2, and a height or a thickness of T2, substantially parallel to the covering portion, the channel-forming portion comprising:
  (i) a first surface and a second surface, the second surface being opposite the first surface at a distance of T2;
  (ii) a first end and a second end, located at each end of the channel-forming portion and the second end opposite the first end at a distance of L2;
  (iii) a microfluidic channel with a length of l, a width of w and a height of h, formed from the first surface toward the second surface and located between the first and second ends and beneath the covering portion, wherein l<L2<L1, w<W2<W1, and h<T2; and
  (iv) openings, located at the second surface, wherein the openings are in fluidic connections with the microfluidic channel,
  wherein the channel-forming portion is in contact with the covering portion at the first and the second ends via the first surface;
(c) a first backing portion and a second backing portion, each having a thickness T3 greater than the channel-forming portion's height T2, located near the first and the second ends of the channel-forming portion and in contact with the second surface thereof; and
(d) an inlet and an outlet, located near the two ends of the microfluidic channel and in fluidic connections with the channel, formed in the channel-forming portion and the backing portions.

In another aspect, the invention relates to a method for forming hanging drops, which comprises: (a) providing a microfluidic hanging drop (μHD) chip as aforementioned; (b) causing a fluid to enter and flow through the microfluidic channel via the inlet; and (c) causing formation of hanging drops (HDs) in the openings, each of the fluidic drops hanging from an opening that contains the fluidic drop. The fluid may be a culture medium. The medium may comprise cells of interest.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 3A-B are not to scale.

DETAILED DESCRIPTION OF THE INVENTION

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, when a number or a range is recited, ordinary skill in the art understand it intends to encompass an appropriate, reasonable range for the particular field related to the invention.

By about 50 to about 500 micrometers it meant that all integer unit amounts within the range are specifically disclosed as part of the invention. Thus, 50, 51, 52, 53 . . . 497, 498, 499 and 500 μm unit amounts are included as embodiments of this invention.

By about 50 to about 1000 micrometers it meant that all integer unit amounts within the range are specifically disclosed as part of the invention. Thus, 50, 51, 52, 53 . . . 997, 998, 999 and 1000 μm unit amounts are included as embodiments of this invention.

By about 1 micrometer to about 2500 micrometer it meant that all integer unit amounts within the range are specifically disclosed as part of the invention. Thus, 1, 2, 3, 4 . . . 2497, 2498, 2499 and 2500 μm unit amounts are included as embodiments of this invention.

A microfluidic device has at least one dimension less than 1 mm. Common fluids used in microfluidic devices include whole blood samples, body fluid, suspensions of microorganisms (such as bacteria, fungus and virus), cell suspensions, protein or antibody solutions and various buffers.

The terms "microfluidic hanging drop chip", "microfluidic chip" and "μHD chip" are interchangeable.

The term "hanging" refers to inclining downward, jutting out, to extend beyond the main body (such as extending beyond the bottom portion and the second surface thereof); projecting; protruding out.

As used herein, the term "droplet" refers to a little drop. The terms "drop" and "droplet" are interchangeable.

The terms "delivering a fluid" and "passing a fluid" are interchangeable.

The term "protrusion part" refers to something that protrudes or projects.

The term "substantially flat" refers to having a surface that is without marked projections.

The term "wells" herein is interchangeable with the term "openings".

The terms "covering portion" and "channel-covering portion" are interchangeable.

Hydrostatic pressure refers to the pressure exerted by a fluid at equilibrium at a given point within the fluid, due to the force of gravity. Hydrostatic pressure increases in proportion to depth measured from the surface because of the increasing weight of fluid exerting downward force from above.

The invention relates to a new microfluidic HD platform that enables control of HD formation, cell loading, media exchange and retrieval of cells without pipette-based manual labor. The invention also relates to a method for the automatic generation of hanging drops (HDs) for sustained three-dimensional (3D) cell culture. HDs emerge automatically through openings at the bottom of a microfluidic channel, which provides a means of and control over the mass transport into and out of the HD. Automatic formation of a row of HDs of various sizes and loading of polystyrene beads and cells into HDs using a microfluidic chip according to the invention were demonstrated. Cells include HL-CZ leukemic cells, human lung cancer cells, mouse embryonic stem cells and mouse embryonic fibroblast cells could be cultured in a microfluidic HD chips for at least 7 days.

Figure 16:
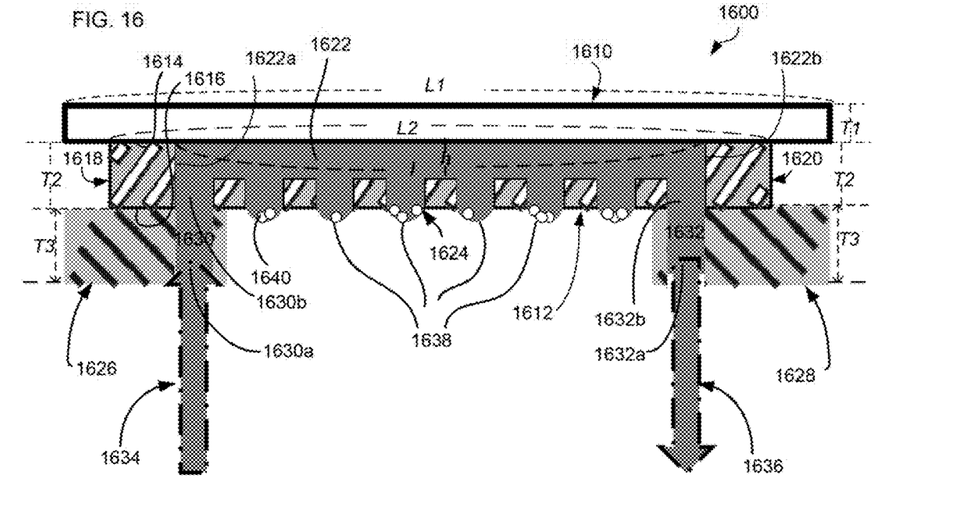
FIG. 16 is a schematic drawing showing a side view of a μHD chip according to one embodiment of the invention.

As shown in FIG. 16, a microfluidic hanging drop chip 1600 comprises:
  (a) a covering portion 1610 with a length, of L1, a width of W1, and a height or a thickness of T1;

(b) a channel-forming portion 1612 with a length of L2, a width of W2, and a height or a thickness of T2, substantially parallel to the covering portion 1610, the channel-forming portion 1612 comprising:
  (i) a first surface 1614 and a second surface 1616, the second surface 1616 being opposite the first surface 1614 at a distance of T2;
  (ii) a first end 1618 and a second end 1620, located at each end of the channel-forming portion 1612 and the second end 1620 opposite the first end 1618 at a distance of L2;
  (iii) a microfluidic channel 1622 with two ends 1622a, 1622b, a length of l, a width of w and a height of h, formed from the first surface 1614 toward the second surface 1616 and located between the first 1618 and second ends 1620 and beneath the covering portion 1610, wherein l<L2<L1, w<W2<W1, and h<T2; and
  (iv) openings 1624, located at the second surface 1616, wherein the openings 1624 are in fluidic connections with the microfluidic channel 1622,
  wherein the channel-forming portion 1612 is in contact with the covering portion 1610 at the first 1618 and the second ends 1620 via the first surface 1614;
(c) a first backing portion 1626 and a second backing portion 1628, each having a thickness T3 greater than the channel-forming portion's height T2, located near the first 1618 and the second ends 1620 of the channel-forming portion 1612 and in contact with the second surface 1616 thereof; and
(d) an inlet 1630 and an outlet 1632, located near the two ends 1622a and 1622b of the microfluidic channel 1622 and in fluidic connections with the channel 1622, formed in the channel-forming portion 1612 and the backing portions 1626, 1628.

The length L1 is defined as the distance between the two ends of the channel-covering portion 1610. The length L2 is defined as the distance between the first 1618 and second ends 1620 of the channel-forming portion 1612. The length l is defined as the distance between the two ends 1622a, 1622b of the channel 1622. The covering portion 1610 is transparent or substantially transparent. The channel-forming portion 1612 is in contact with or bond to the covering portion 1610 via the first surface 1614. The openings may be in a row or in an array. The first backing portion 1626 and the second backing portion 1628, located near the first 1618 and second ends 1620 of the channel-forming portion, respectively, are bonded onto the second surface 1616 of the channel-forming portion 1612. Tubes 1634, 1636 may be connected to the inlet 1630 and outlet 1632. The hanging drops 1638 form in the openings 1624. Cells 1640 dock in the hanging drops 1638.

To form hanging droplets, a fluid is delivered into the channel and filled the channel's space first (i.e., the first layer), then filled the openings (i.e., the second layer). When the layer 2 was not filled, the openings appeared darker under the stereomicroscope due to light refraction deflection. When the second layer was fill with the fluid, the dark shadow disappeared. After all the openings were filled with the fluid, further fluids were made to flow through the channel, which caused the formation of hanging drops. When the surface tension of a hanging droplet was overcome by the fluid pressure, the hanging drop burst, which caused other droplets shrink in volume due to loss of fluid to the burst hanging droplet. A burst hanging droplet means a hanging drop that hangs from the opening and extends toward the second surface of the channel-forming portion. A burst droplet (or drop) has a greater diameter than the opening from which it hangs, In one aspect, the invention relates to a microfluidic hanging drop (μHD) chip, which comprises:
  (a) a covering portion with a length of L1, a width of W1, and a height or a thickness of T1;
  (b) a channel-forming portion with a length of L2, a width of W2, and a height or a thickness of T2, substantially parallel to the covering portion, the channel-forming portion comprising:
    (i) a first surface and a second surface, the second surface being opposite the first surface at a distance of T2;
    (ii) a first end and a second end, located at each end of the channel-forming portion and the second end opposite the first end at a distance of L2;
    (iii) a microfluidic channel with a length of l, a width of w and a height of h, formed from the first surface toward the second surface and located between the first and second ends and beneath the covering portion, wherein l<L2<L1, w<W2<W1, and h<T2; and
    (iv) openings, located at the second surface, wherein the openings are in fluidic connections with the microfluidic channel,
    wherein the channel-forming portion is in contact with the covering portion at the first and the second ends via the first surface
  (c) a first backing portion and a second backing portion, each having a thickness T3 greater than the channel-forming portion's height T2, located near the first and the second ends of the channel-forming portion and in contact with the second surface thereof; and
  (d) an inlet and an outlet, located near the two ends of the microfluidic channel and in fluidic connections with the channel, formed in the channel-forming portion and the backing portions.

In one embodiment of the invention, the second surface of the channel-forming portion is substantially flat and/or is without protrusion parts thereon. The aforementioned μHD chip may comprise more than one microfluidic channel. The channels may or may not have the same size of openings at the bottom thereof. The openings are connected to a channel without a barrier present between the openings and the channel that is connected to the openings. The openings are open to the air and accessible from the bottom of the chip, that is, from the second surface of the channel-forming portion. The μHD chip may comprise an array of openings.

In one embodiment of the invention, the aforementioned μHD chip comprises multiple channels with each channel in fluidic connections with openings that are arranged in a row.

In another embodiment of the invention, each opening has a diameter ranging from 1 micrometer to 2500 micrometer.

In another embodiment of the invention, the diameter of the openings ranges from 50 micrometer to 1 mm.

In another embodiment of the invention, the covering portion is not adapted to be removable from the channel-forming portion.

The aforementioned μHD chip may further comprises a cell culture medium, located within the microfluidic channel and the openings, wherein the cell culture medium within the openings forms hanging drops. The hanging drops may contain cells. The μHD chip may further comprise a fluid delivery device in a fluidic connection with the inlet and a fluid sucking device in a fluid connection with the outlet.

In another embodiment of the invention, the channel-forming portion comprises a material selected from the group consisting of polyditmethyl-siloxane (PDMS), Polyethylene (PE), Polycarbonate (PC), Polystyrene (PS), Polymethyl methacrylate (PMMA). Cyclic Olefin Copolymer (COC), silicon, glass and thermoplastics materials. In another embodiment of the invention, the first surface of the channel-forming portion at the first and the second ends thereof is bonded to the covering portion.

Further in another embodiment of the invention, the μHD chip is placed inside a container. The container may comprise a liquid reservoir. The container may further comprises an external inlet which is in a fluidic connection with the inlet of the μHD chip; and an external outlet opposite the external outlet and in a fluidic connection with the outlet of the μHD chip. The external inlet of the container may be in a fluidic connection with a fluid delivery device and the external outlet may be in a fluidic connection with a fluid sucking device.

In another aspect, the invention relates to a method for forming hanging drops, which comprises: (a) providing a microfluidic hanging drop (μHD) chip as aforementioned; (b) causing a fluid to enter and flow through the microfluidic channel via the inlet; and (c) causing formation of hanging drops (HDs) in the openings, each of the fluidic drops hanging from an opening that contains the fluidic drop. The fluid may be a culture medium. The medium may comprise cells of interest. The aforementioned method may further comprise allowing an additional fluid to exit from the outlet.

The aforementioned method may further comprise placing the chip in a container, the container comprising a holder adapted to accommodate the chip.

In one embodiment of the invention, the fluid comprises cells in suspension and the hanging drops comprises the cells.

In another embodiment of the invention, each hanging drop has a height H of no greater than the diameter of the opening containing the hanging drop. The height H of hanging drop may be controlled by varying the hydrostatic pressure of the fluid. The hydrostatic pressure depends on the difference in the altitude between the liquid level in the bottle connected to the inlet and the level of the μHD chip (Δh shown in FIG. 7). The pressure is calculated using the equation P=ρgh, where P is pressure ($N/m^2$), ρ is density of liquid ($kg/m^3$), g is gravity ($998 kg/m^3$) and h is height difference (Δh shown in FIG. 7).

Further in another embodiment of the invention, the step of causing the fluid to enter and flow through the microfluidic channel via the inlet is performed under a hydraulic pressure or by a pump.

Yet in another embodiment of the invention, the hanging drops do not extend beyond the openings or to the second surface of the channel-forming portion.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Methods and Materials

The device comprises a microfluidic channel incorporating openings at its bottom and is fabricated in polydimethylsiloxane (PDMS) on glass substrates using soft lithographic and PDMS membrane transferring techniques. Briefly, master wafers with two-layer features were made using conventional photolithography with a negative photoresist (SU-8, Microchem Inc., Newton, Mass.). The masters were then used as molds, on which PDMS prepolymer was poured. A fluoropolymer coated polyester (PE) sheet (Scotchpark™ 1002 Release Liner, 3M™, St. Paul, Minn.) and thick (thickness 1 cm) glass were applied and pressed against the master to squeeze out excess PDMS. The PDMS was allowed to cure in a conventional oven at 65 C for 2 h. Once cured, PDMS features along with the adhered PB sheet were removed from the master. The PDMS layer was bonded to a glass substrate after both being treated with oxygen plasma and the PE sheet was peeled off.

HDs were generated in the openings at the bottom of the PDMS microchannel when solutions were introduced into the microchannel at a controlled flow rate by using hydrostatic pressure or a syringe pump. The minimum pressure (pressure at which droplets begin to form) and maximum pressure were evaluated. When droplets burst, at least one droplet extends to the second surface and the fluids in other droplets flow to the burst droplet/s, thus, they appear to be flatten. Thus, the relationship of the diameter of the opening and the burst pressure was evaluated as the applied pressure was increased until the HD becomes flattened.

Figure 3A:
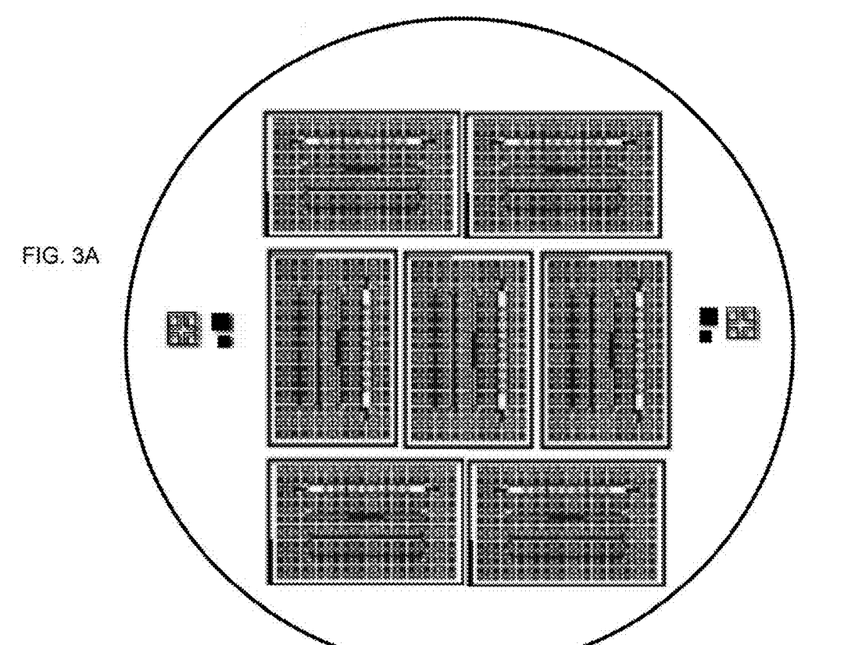
FIGS. 3A-B show designs of a master wafer. A: a mask design with 7 small pieces of wafers (i.e., molds). B: an enlarged view of a master wafer of FIG. 3A, showing the diameters of the openings from the bottom to the top: 50, 100, 200 and 500 μm.
Figure 3B:
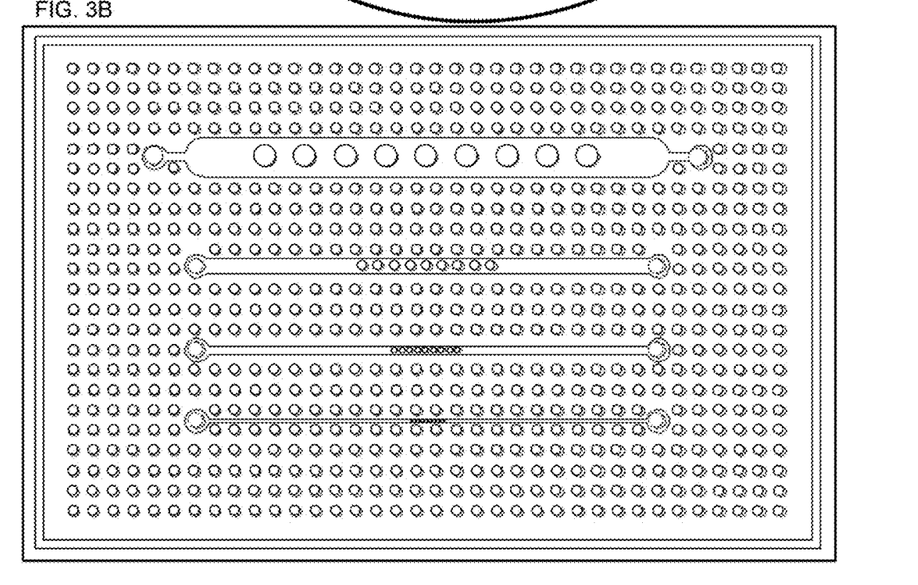
Figure 4A:
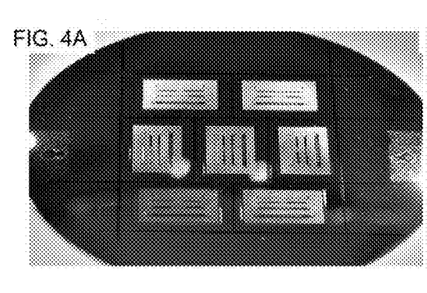
FIGS. 4A-B show a large wafer with seven smaller wafer pieces containing SU8 structures after soft lithography fabrication, and the seven smaller pieces for clamp-molding process.
Figure 4B:
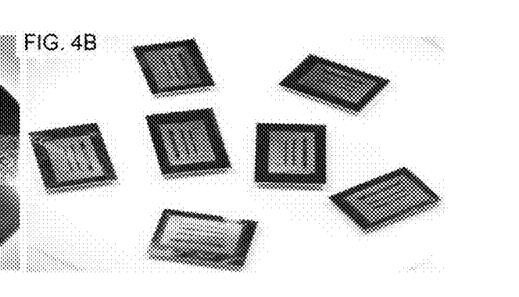

FIGS. 3-5 show the fabrication process of μHD chips of the invention.

Photolithography

Below lists steps of photolithography for printing patterns on a photomask to a wafer.

Step 1: coat SU-8 50 photoresist on wafer: spread 500 rpm, 5 sec, then spin 1250 rpm, 30 sec.

Step 2: soft bake: 65° C., 10 min, then 95° C., 20 min.

Step 3: exposure for 2.5 sec.

Step 4: Post-bake: 65° C., 10 min, then 95° C., 10 min.

Step 5: Washing aligner key (left and right symmetric, two sets)

Step 6: Coat SU-8 50 on water: spread 500 rpm, 5 sec, then 1800 rpm, 30 sec.

Step 7: soft bake: 65° C., 20 min, then 95 C, 10 min.

Step 8: Align key (mask and wafer)

Step 9: Exposure: 2.5 sec.

Step 10: Post-bake: 65° C., 8 min, then 95° C., 10 min.

Step 11: Washing wafer.

Step 1-4 is the layer 1 structure. Step 6-9 is the layer 2 structure.

The cleaning liquid is propylene glycol mono-methyl ether acetate (PMA). The parameters are all real number in this illustrated example.

Preparation of a PDMS Device

FIG. 4A show a wafer with protruding features (SU8 structure) after soft lithography fabrication, in which the layer 1 feature has a thickness (height, Y1) of 100±1 μm, and the layer 2 feature a thickness (height, Y2) of 130±2 μm. FIG. 4B show 7 small pieces of master wafers. Each master wafer was used as a mold that is coated with silane (surface treatment, which would assist later on peeling off of PDMS from the mold). Master wafers were then placed in oxygen plasma for 2 minutes and placed them together with 2 drops of trichlorosilane (in a weighting dish) in a desiccator for 30 minutes. After the coating, each master wafers would have a monolayer of silane coating.

Figure 5A:
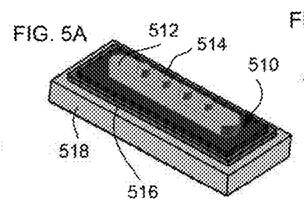
FIGS. 5A-H show a clamp-molding process for fabrication of a μHD chip.

FIGS. 5A-H show a clamp-molding process for fabrication of a PDMS device 500:

FIG. 5A) Place a thin cured (solid) PDMS sheet 516 on a thick (height=1 cm) glass 518. Place a master wafer 510 (with SU 8 channel mold 512 and openings' mold 514 structures) on top of the thin PDMS sheet 516.

Figure 5B:
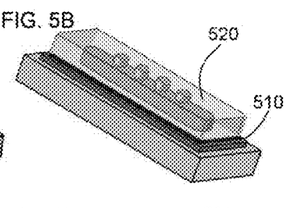

FIG. 5B) Pour uncured (liquid) PDMS 520 on the wafer 510 and ensure the surface of the wafer 510 is coated with the liquid PDMS 520.

Figure 5C:
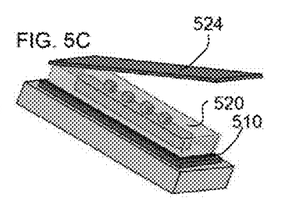

FIG. 5C) Apply a piece of PE sheet 524 onto the uncured PDMS 520 and wafer 510.

Figures 5D, 5E, 5F, 5G, 5H:
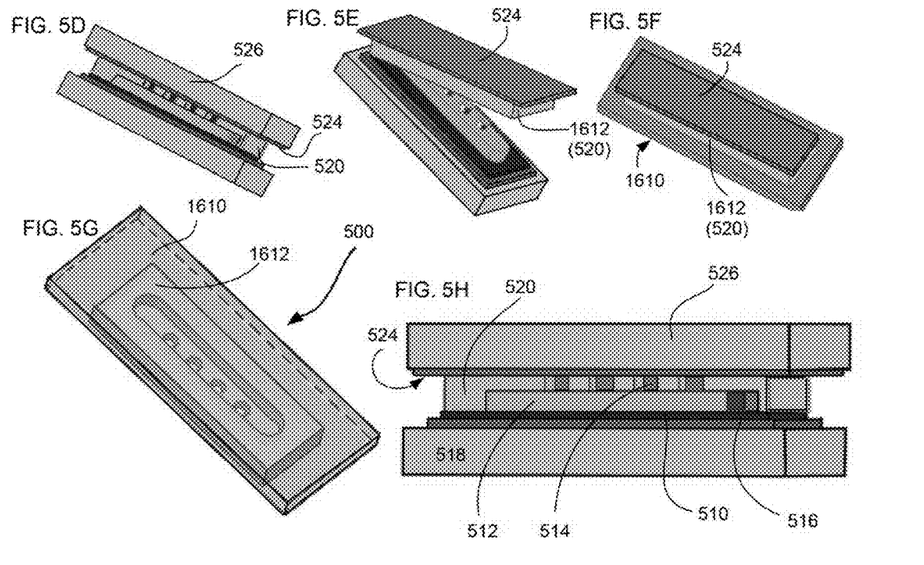

FIG. 5D) Place another thick (1 cm) glass 526 on top of the PE sheet 524, place it in an oven of 65° C. for 2 hr.

FIG. 5E) After the PDMS 520 is cured, removing the glass 526, release the PE sheet 524 with the PDMS membrane 520 attached thereto. The areas where there were SU 8 channel mold 512 and openings' mold 514 structures are hollow and areas without structures are cured (solid) PDMS 520 (which would serve as a channel-forming portion 1612). Place the cured PDMS membrane 520 with the PE sheet 524 attached thereto and a new piece of glass slide 1610 (1"×3", height=1 mm) in an oxygen plasma machine for a two-minute treatment with the PDMS 520 (or channel-forming portion 1612) facing up and PE sheet 524 facing down) for an efficient treatment.

FIG. 5F) After oxygen plasma treatment, bond the PDMS membrane 520 (or the channel-forming portion 1612) onto the new glass slide 1610 (the side that is faced up during the oxygen plasma treatment) by placing the PDMS membrane 520 (or the channel-forming portion t612) on the glass slide 1610 (which would serve as a channel-covering portion). Place the bond PDMS-glass slide onto a hot plate (65° C.-75° C.) for 20 minutes to enhance bonding.

FIG. 5G) Peel off the PE sheet 524 from the PDMS membrane 520 (or the channel-forming portion 1612). A PDMS device with the covering portion 1610 and the channel-forming portion 1612 is made.

FIG. 5H) A cross section view of the clamp-molding setup: A thick glass (1 cm) on the top 526, then PE sheet 524, PDMS membrane (with channels and openings) 520, SU 8 channel 512 and opening 514 structures, silicon wafer 510, thin PDMS sheet 516, and a thick glass (1 cm) 518 at the bottom.

Formation of Inlet and Outlet

Preparation prior to fabrication of inlet and outlet: About 35 g of PDMS prepolymer solution in a 15 cm-dish was placed inside a 65° C. oven for 6 hours to cure the PDMS. The cured (solidified) PDMS was cut into square blocks (1×1 cm, height 0.3 cm). The PDMS block would serve as the first and second backing, portions 1626, 1628.

Figures 6A, 6B, 7:
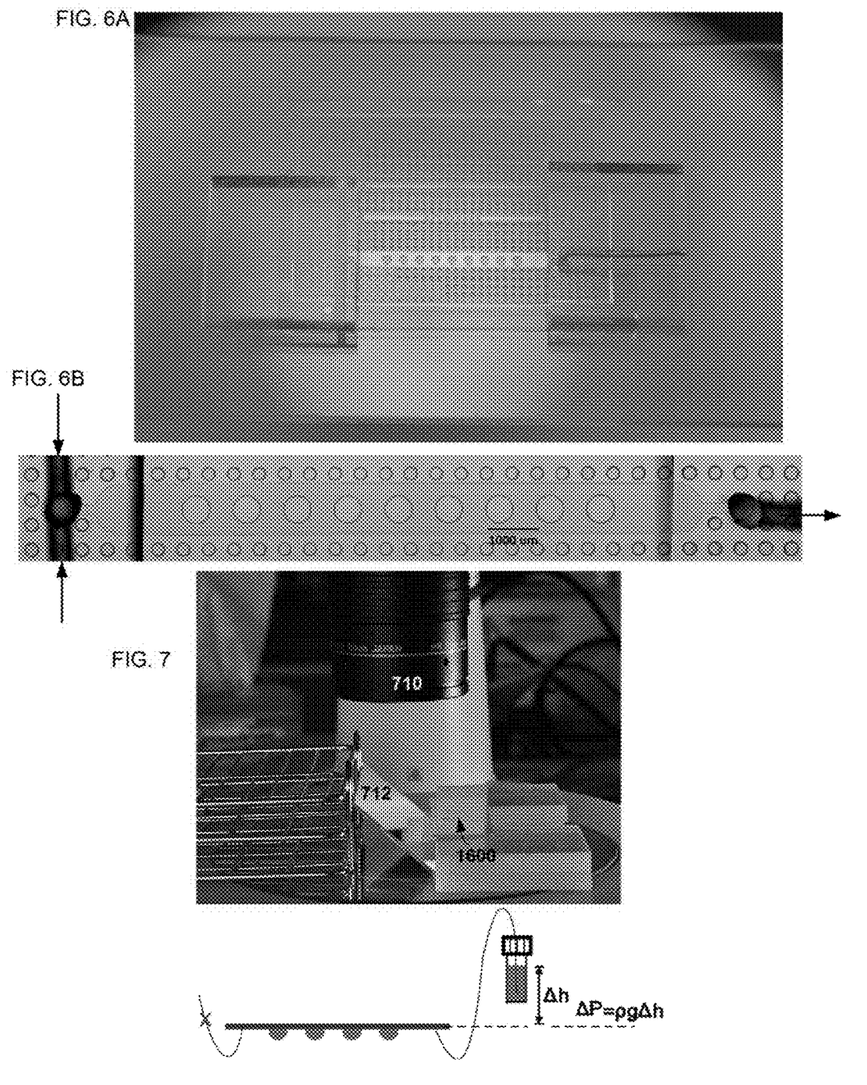
FIGS. 6A-B are microphotographs showing an inverted view and an enlarged section of a μHD chip. Scale bar: 1000 μm.
FIG. 7 is a photograph showing the arrangements of devices for observation of hanging droplet formation at the openings of the chip under various pressures.
Figure 17A:
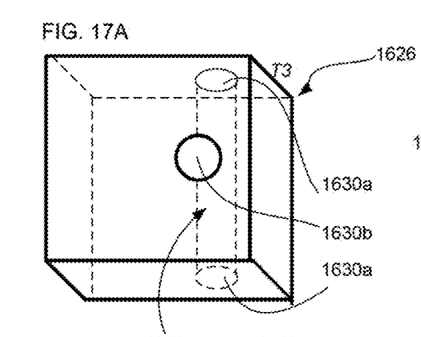
FIGS. 17A-D are schematically drawings showing the process of formation of inlet and outlet.
Figure 17B:
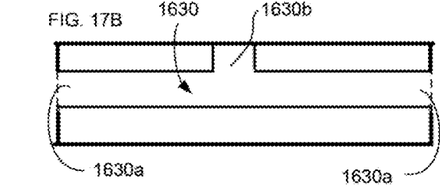

FIGS. 17A-B show the process of forming inlet 1630. Using a puncher (a sharpened blunt needle) to punch a straight channel (an inlet channel) 1630, which would serve as an inlet 1630, through a piece of PDMS block 1626 (1×1 cm, height 0.3 cm) from the side (FIG. 17A). The straight channel 1630 is for tubing insertion. It has two ends for inserting two separate tubes. One tube is used for delivering a cell suspension and the other tube is used for connecting to a bottle containing a fresh medium (as shown in FIG. 6B). Then punching a hole 1630b from the top of the PDMS block 1626, in which the hole 1630b is in a fluidic connection with and perpendicular to the inlet channel 1630. The inlet PDMS block 1626 would serve as a first backing portion 1626. Tubes may be connected to the inlet channel (or inlet) 1630 via the holes 1630a at the two ends of the inlet channel 1630 for delivering cells and/or fresh medium. FIG. 17B is a side view showing the hole 1630b perpendicular to and in a fluidic connection with the inlet channel 1630.

Figure 17C:
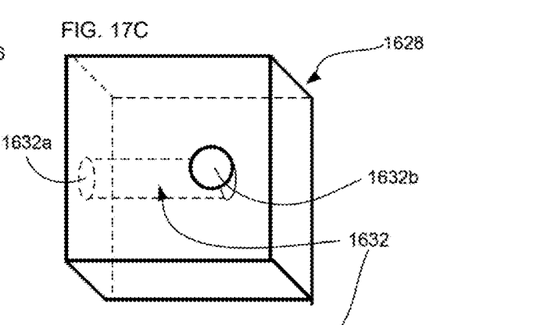
Figure 17D:
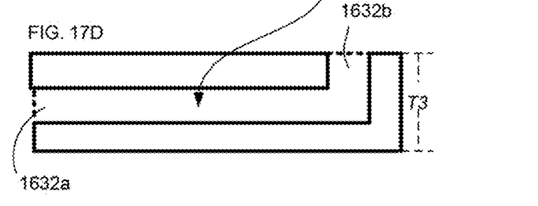

FIGS. 17C-D show the process of forming outlet 1632. Punching a straight channel 1632 (an exit channel) half-way through (not all the way through) a piece of PDMS block 1628 (1×1 cm, height 0.3 cm) from the side (FIG. 17C). Then punching a hole 1632b from the top of the PDMS block 1628, in which the hole 1632b is perpendicular to and in a fluidic connection with the enclosed end of the exit channel 1632.

FIG. 17D is a side view showing the hole 1632b in a fluidic connection with and perpendicular to the enclosed end of the outlet channel 1632.

After the inlet and outlet blocks (which are the first and second backing portions 1626, 1628) were made, placing them (with the punched hole 1630b, 1632b facing up) and the previously made PDMS membrane with a glass slide (which is the covering portion 1610) attached thereto (with the PDMS membrane facing up) into an oxygen plasma machine for 2 minute treatment. The previously made PDMS membrane also has two holes 1630b, 1632b made thereon. After the treatment, inverting the inlet block 1626 and match its hole 1630b with the one 1630b on the PDMS membrane (the channel-forming portion 1612) near the first end 1618 thereof. The hole 1630b on the PDMS membrane 1612 is in a fluidic connection with the microfluidic channel 1622. Repeating the process for the outlet block 1628 to match its hole 1632b with the one 1632b on the other end of the PDMS membrane 1612. The holes 1630b on the inlet block 1626 and the channel-forming portion 1622, and the two open ends 1630a of the inlet channel 1630 on the inlet block 1626 together form the inlet 1630 of the chip 1600. The holes 1632b on the exit block 1628 and the channel-forming portion 1622, and the open end 1632a of the exit channel 1632 on the exit block 1628 together form the exit 1632 of the chip 1600. Place the chip on a 65° C. hotplate for at least 2 hours. A micro-hanging drop (μHD) chip 1600 is completed.

The two holes 1630b, 1632b (which serve as inlet and outlet, respectively) in the previously made PDMS membrane are fabricated during the clamp molding process. As shown on FIG. 3B, at each end of the channel, two circles are bridged to the channel. The outer circle shares the same height as the channel and the inner circle serves as protruding poles, which have the same height as layer 2 (i.e. the opening). Thus, there will be two openings at the end of each channel.

The μHD chip is placed in an enclosed environment for cell culture. The enclosed environment, in this case a 10 cm dish, is filled with liquid at the bottom, thus the atmosphere is humidified. The dimensions listed below are for illustration purpose only. Other dimensions that are suitable for forming μHD chips and formation of HDs may be used.

Dimensions of PDMS: PDMS membrane is 12.7×19.4 mm. The **thickness of the PDMS membrane is 230 μm (thickness of layer 1 plus layer 2=100+130=230).

Dimensions of channels: Channel with 500 μm opening: Length=13.5 mm; width 1 mm (1000 μm); thickness=100 μm. Channel with 200 μm opening: 2.2.1 Length=11.4 mm; width=0.6 mm (600 μm); thickness=100 μm. Channel with 100 μm opening: 2.3.1 Length=11.4 mm; width=0.2 mm (200 μm); thickness=100 μm. Channel with 50 μm opening: 2.4.1 Length=11.4 mm; width=0.1 mm (100 μm); thickness=100 μmm.

The thickness of the PDMS membrane may be varied. It is feasible to alter the thickness of layer 1 (i.e., thickness of microchannel) and layer 2 (thickness of the opening) during SU8 photolithography process.

Dimensions of the thicker PDMS for inlet and outlet blocks: Length=1 cm; Width=1 cm; thickness=3 mm.

Assembly of Microfluidic Hanging Droplet Platform

A 10-cm culture plate cover was drilled to make three holes, where two holes are across each other and the third hole is perpendicular to the midpoint of the other two holes. The bottom of a 10-cm culture dish are filled with 7 ml of internal reservoirs. The culture plate further comprises two external holders adapted to holding inlet and outlet fluid reservoirs. The culture plate further includes a chip holder (such as pieces of 4 mm thick PDMS block to hold a μHD chip)

allowing formed droplets be close to the internal reservoirs. The height of the PDMS block (or chip holder) has a lower height than that of the 10-cm culture dish. Place the μHD chip onto the chip holder (4 mm thickness PDMS) and enclose the dish with the drilled plate. Passing a fluid comprising cells in suspension into the chip placed on the chip holder to form hanging drops loaded with cells. After the cells are loaded into hanging drops, the inlet is in a fluidic connection with an external inlet reservoir comprising a fresh media. The outlet of the channel is in a fluidic connection with an external outlet reservoir. The pressure permits a continuous and steady supply of the fresh media to the channel and hanging drops comprising the cells. The tubes connected to the external inlet reservoir and the inlet of the channel-forming portion were properly placed inside the holes on the 10-cm culture plate's cover.

To seed cells or beads, cell or bead suspension was flowed through the channel and the flow was stopped for 5 min to allow the cells or beads to settle into HDs. Excess cells were removed by restarting the flow.

Results

A microfluidic device was developed for the automatic generation an easy fluidic access. Hanging drops or droplets (HDs) were formed in the openings at the bottom of the microchannel. The diameter of the opening may range from 1 to 2500 μm.

The relationship of the diameter of the opening and the burst pressure was evaluated. The burst pressure is defined as the pressure at which the HD becomes flattened. As a qualitative assessment considering only convective transport, the maximal rate to replenish the solution in the HD can be calculated as the diameter of the opening divided by the mean velocity in the microchannel. The solution at the opening could be replenished for more than 50 times in one second even for the openings as large as 500 μm in diameter, which is adequate for a typical cell culture. Polystyrene beads of 10 μm in diameter and cells including human lung cancer cells, mouse embryonic stem cell and mouse embryonic fibroblast were successfully loaded into HDs.

Figure 1A:
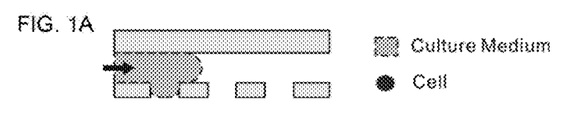
FIGS. 1A-D are schematic drawings showing cross-sections of a microfluidic hanging drop (μHD) chip and its operation principle.
Figure 1B:
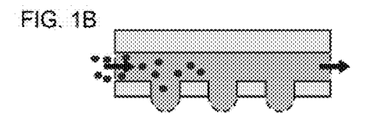
Figure 1C:
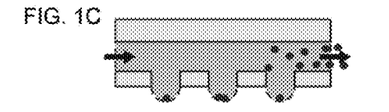
Figure 1D:
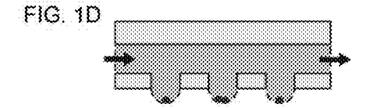

FIGS. 1A-D show a cross-section of a μHD chip in operation FIG. 1A: A medium enters and fills the microchannel. FIG. 1B: when the microchannel is filled with the medium, pendent drops are formed and hang at the bottom of the openings. Cells are loaded into the microchannel and lock in the hanging drop (HD). FIG. 1C: Untrapped cells can be rinsed off. FIG. 1D: Different extracellular solutions can be introduced into the HD through the microchannel under the precise temporal and spatial control. Cells cultured in the HD can be either harvested directly from the HD using a micropipette or collected at the outlet by applying suction to the microchannel.

To transfer cells, one can increase the applied pressure by raising both inlet and outlet bottle. As the pressure increases, micro-hanging droplets (μHDs) would burst on the outer surface of the PDMS membrane (i.e., the second surface 1616 of the channel-forming portion 1612) and the cells can be harvested by suction or rinsing off with a medium from the air-droplet interface (i.e., from the outer surface of the PDMS membrane, or from the second surface 1616 of the channel-forming portion 1612) using a micropipette.

Figure 2A:
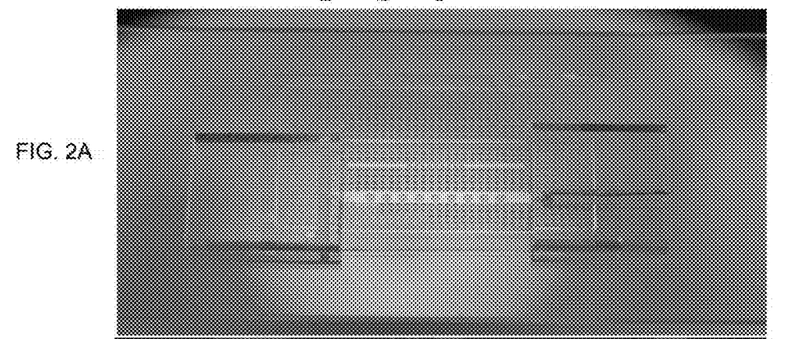
FIGS. 2A-B are photographs showing an inverted view of μHD chips. A: A μHD chip with channels and openings of various diameters. B: An arrayed μHD chip with 9 channels, 26 openings per channel, each opening in a diameter of 1 mm (1000 μm) (an array of 9×26 wells).
Figure 2B:
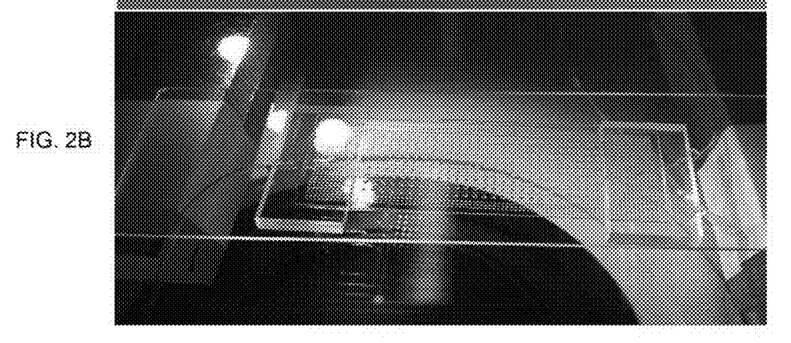

FIG. 2A shows an inverse view of a μHD chip with channels and wells (or openings) of various diameters from the bottom to the top: 500 μm, 200 μm, 100 μm, and 50 μm, respectively. FIG. 2B shows an inverse view of a μHD chip with 9 channels, each channel in fluidic connections with 26 openings located at the bottom of the channel forming portion, each opening having a diameter of 1000 μm (1 mm).

FIG. 3A shows a mask design of 7 master wafers on a 4" silicon wafer (outer circle). Each wafer may serve as a mold for making a μHD chip. FIG. 3B is an enlarged view of a master wafer, showing longitudinal protruding features, which would form channels (designated as layer 1 feature with a height of Y1), and small round features protruding from the longitudinal features (designated as layer 2 feature with a height of Y2, and Y2>Y), which would form the openings. The small round features from the bottom to the top would form openings with diameters of 50, 100, 200 and 500 μm. Supporting features are located among the longitudinal protruding features and have the same height Y2 as the layer 2 features. FIGS. 3A-B are not to scale.

FIG. 6A show a whole view of an inverse μHD chip. An enlarged view in FIG. 6B shows the channel and the openings with a diameter of 500 μm, the inlet connected to two tubes (indicated by downward and upward arrows), one for delivering cells of interest, the other for delivering a fresh medium, and the outlet connected to an outgoing tube (indicated by a rightward arrow).

Figure 8A:
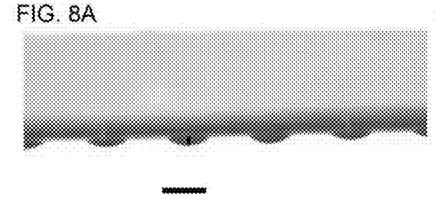
FIGS. 8A-D are side views showing droplet formation in a p-D chip with an opening diameter of 500 μm under various pressure. The vertical bar indicates the height of the hanging drop, A: droplet height 86.58781, μm at the pressure 205.8 N/ml$^2$; B: droplet height 134.4584 μm at 279.3 N/m$^2$; C: droplet height 191.8916 μm at 352.8 N/m$^2$; D: burst droplet (arrow) at 401.8 N/m$^2$. Scale bar: 500 μm.
Figure 8B:
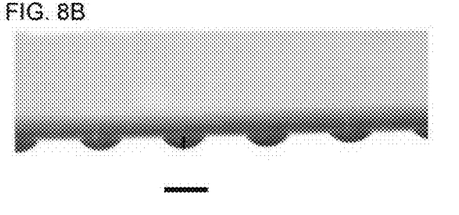
Figure 8C:
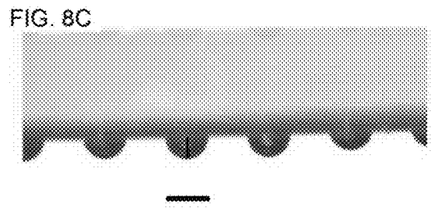
Figure 8D:
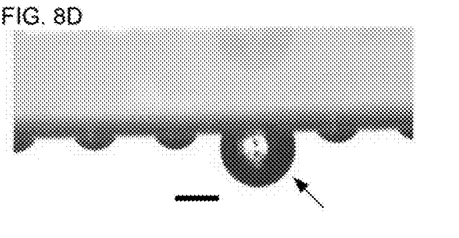
Figure 9A:
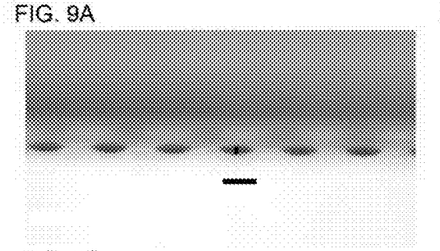
FIGS. 9A-D are side views showing droplet formation in a μHD chip with an opening diameter of 200 μm under various pressure. The vertical black bar within the droplet indicates the size/height of the hanging drop. A: droplet height 33.58103 μm at the pressure 343 N/m$^2$; B: droplet height 44.80326 μm at 416.5 N/m$^2$; C: droplet height 8.16841 gμm at 539 N/m$^2$; and D: burst droplet (arrow) at 563.5 N/m$^2$. Scale bar: 200 μm.
Figure 9B:
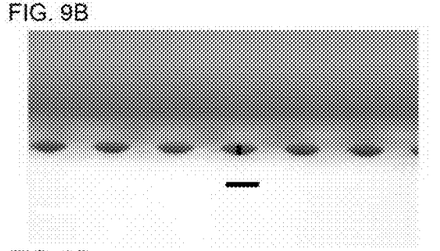
Figure 9C:
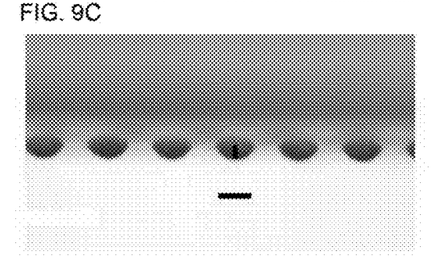
Figure 9D:
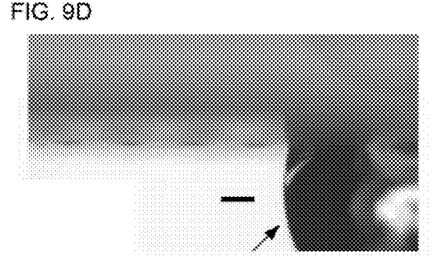

FIG. 7 shows arrangements of devices for observation of the relationship between the height of the droplets (openings of various diameters) and hydrostatic pressure. A μHD chip 1600 was placed on the platform of a stereomicroscope 710 near the objective lens, and a mirror 712 was placed in front of the μHD chip 1600 and under the objective lens. This arrangement allowed the stereomicroscope to capture the images from the side. The heights of droplets in a μHD chip with the opening diameter of 500 μm were 86.58781 μm (FIG. 8A), 134.4584 μm (FIG. 8B), 191.8916 μm (FIG. 5C), and burst droplet (FIG. 8D) at the hydrostatic pressure of 205.8 N/ml$^2$, 279.3 N/m$^2$, 352.8 N/m$^2$, and 401.8 N/m$^2$, respectively. The heights of droplets In a μHD chip with the opening diameter of 200 μm were 33.58103 μm (FIG. 9A), 44.80326 μm (FIG. 9B), 83.16841 μm (FIG. 9C), and burst droplet (FIG. 9D), at the pressure of 343 N/m$^2$, 416.5 N/m$^2$, 539 N/m$^2$, and 563.5 N/m$^2$, respectively.

Figure 10A:
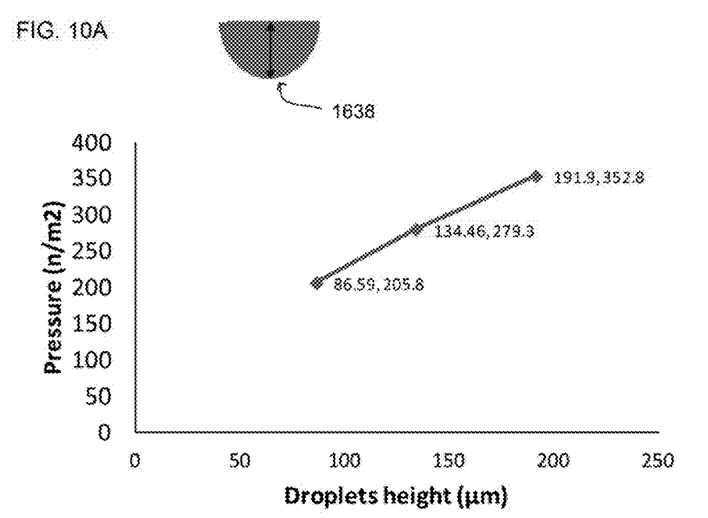
FIGS. 10A-C show the relationship of the hanging droplet height versus pressure.
Figures 10B, 10C:
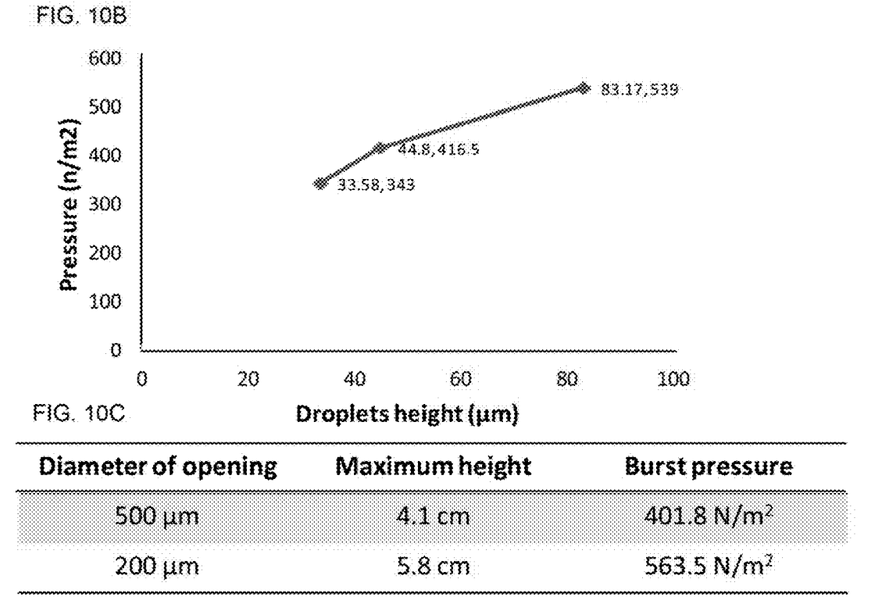
Figure 11A:
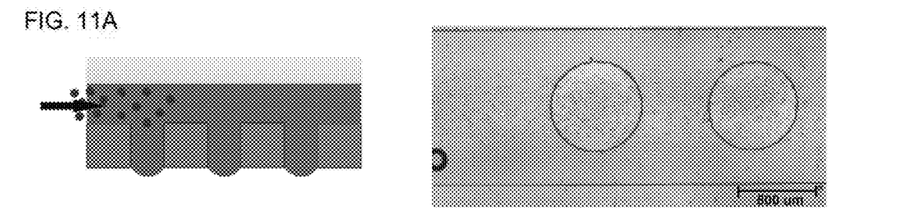
FIGS. 11A-D are schematic cross-section view of a μHD chip (left panels) and micrographs of hanging droplets viewed from underneath (right panels) showing culture of mouse embryonic stem cells using a μHD chip method according to the invention. Scale bar: 500 μm.
Figure 11B:
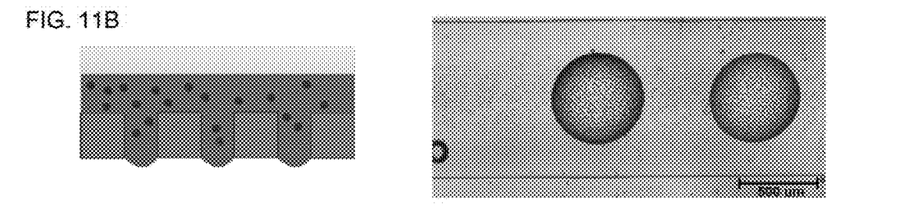
Figure 11C:
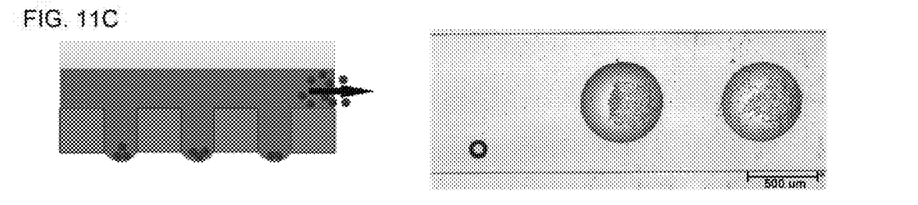
Figure 11D:
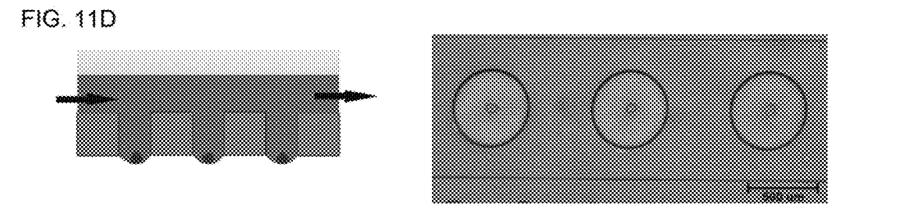

FIGS. 10A-C show the relationship of droplet's heights versus hydrostatic pressure. The height of the droplet is defined as the length of the protruding droplet as shown in FIGS. 8-9 (vertical bars within the droplets). A droplet's height is measured from the edge of the PDMS film (i.e., the second surface of the channel-forming portion) to the bottom point of the outward curvature of the droplet. Images of sagittal-plane-droplets were taken by a stereomicroscope, which was connected to a computer. The captured images of sagittal-plane-droplets were analyzed and measured by QCapturePro software, which controlled the camera connected to the stereomicroscope. The setup of the stereomicroscope and devices is shown in FIG. 7. The hydrostatic pressure depends on the difference in the altitude between the liquid level in the bottle and the level of the HD chip (Ah shown in FIG. 7). The pressure is calculated using the equation P=pgh, where P is pressure (N/m$^2$) p is density of liquid (kg/m$^3$), g is gravity (998 kg/m$^3$) and h is height difference (Ah shown in FIG. 7).

Figure 12A:
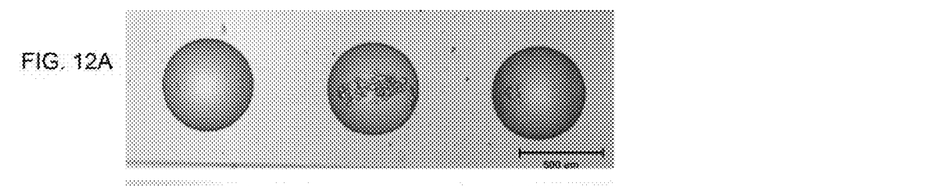
FIGS. 12A-C are micrographs of hanging droplets viewed from underneath, showing mouse embryonic fibroblast cell aggregate formation at different time points using a μHD chip method. A: 0 hr; B: 18 hr; C: 25 hr.
Figure 12B:
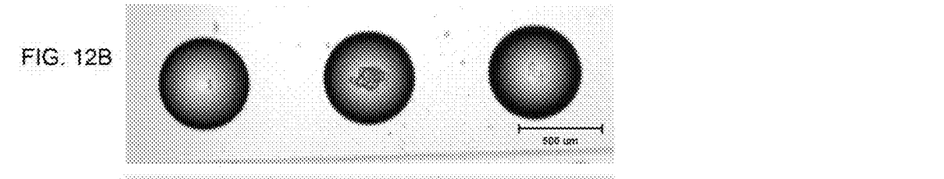
Figure 12C:
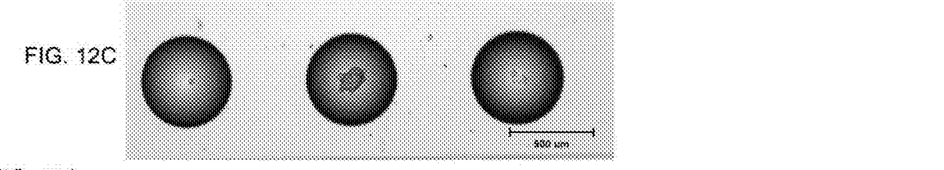

FIG. 11 shows cell culture and cell aggregate formation in 500 μm-diameter wells (openings in a row) in μHD chips. The left panels are schematic cross-section views of a μHD chip, the right panels a top-down view micrographs (right panels). Cells were mouse embryonic stem cells. A: Loading cells into the channel of the μHD chip; B: stopping flow to let cells descend; C: restarting flow to wash away excess cells; D: cells growing in the μHD chip under perfusion of medium. FIG. 12 show mouse embryonic fibroblast cell aggregate formation at different time points, 0 hr, 18 hr and 25 hr (A-C, respectively), using a μHD chip method.

Figure 13A:
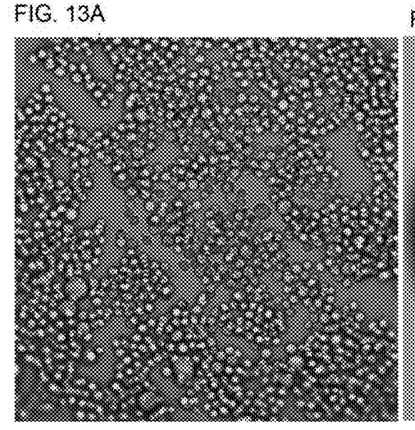
FIGS. 13A-B are microphotographs of hanging droplets viewed from underneath, showing human lung cancer cell aggregate formation. A: 1-hour cell culture using a conventional HD method; B: 0-hr cell culture using a μHD chip method. Scale bar: 200 μm.
Figure 13B:
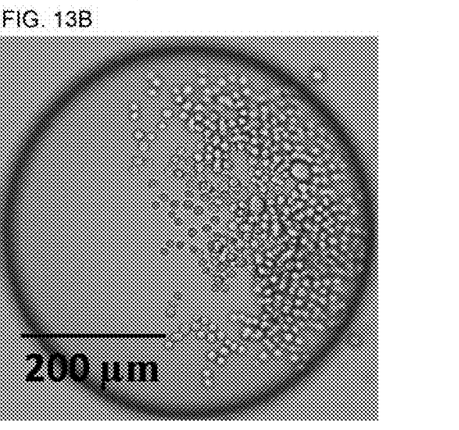

FIGS. 13A-B show human lung cancer cell aggregate formation using the conventional HD method in an one-hour cell culture and a μHD chip method in a 0-hour cell culture, respectively.

Cells cultured with the conventional HD method distributed in the droplets at time 0, and took time (about 1 hr) to centralize in the droplet. Cells cultured in the μHD chip centered in the droplets rapidly. Therefore, cells cultured for 1 hour with the conventional HD method were more comparable to the cells cultured for 0 hr with the a μHD chip.

Figure 14A:
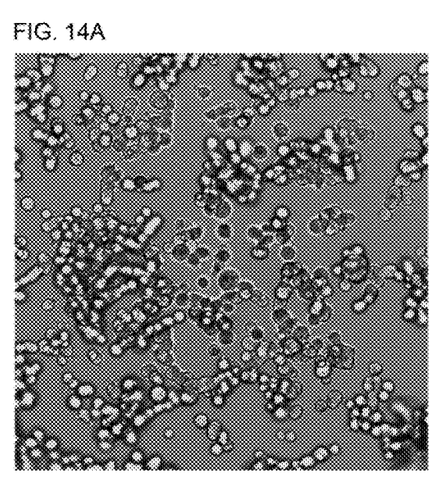
FIGS. 14A-B are microphotographs of hanging droplets viewed from underneath, showing human lung cancer cell aggregate formation in a 24-hour cell culture. A: conventional HD method; B: μHD chip method. Scale bar: 200 μm.
Figure 14B:
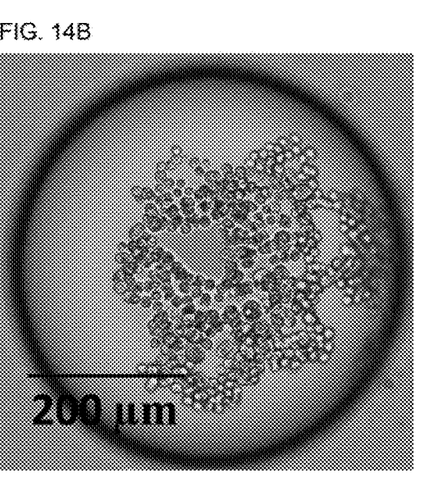
Figure 15A:
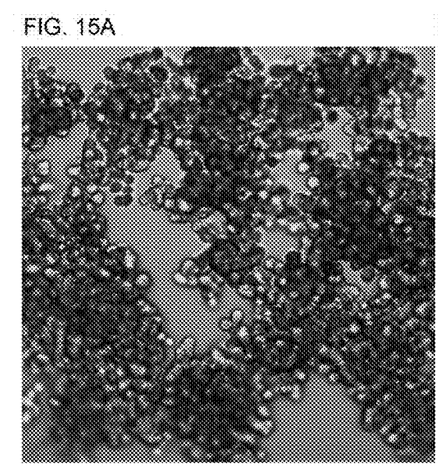
FIGS. 15A-B are microphotographs of hanging droplets viewed from underneath, showing human lung cancer cell aggregate formation in a 48-hour cell culture. A: conventional HD method; B: μHD chip method. Scale bar: 200 μm.
Figure 15B:
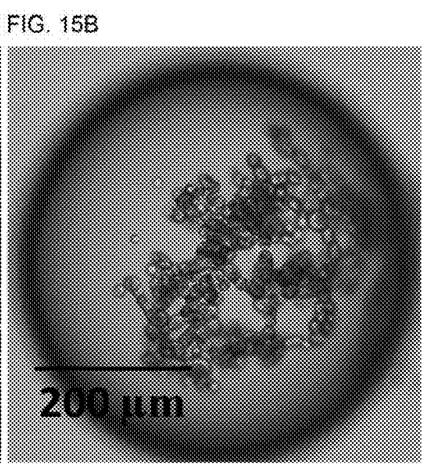

FIGS. 14 and 15 show human lung cancer cell aggregate formation in a 24-hr (FIGS. 14A-B) and 48-hr (FIGS. 15A-B) cell culture using the conventional HD method (FIGS. 14A and 15A) and the μHD chip method (FIGS. 14B and 15B).

In conclusion, we invent and demonstrate a simple microfluidic HD cell culture platform. The integration of microfluidic channel to the HD allows automation, and high-throughput, long-term 3D cell culture, which is expected to be beneficial for the studies, such as stem cell differentiation, regenerative medicine, tissue engineering, drug screening and developmental biology.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A microfluidic hanging drop chip comprises:
   (a) a covering portion with a length of L1, a width of W1, and a height or a thickness of T1;
   (b) a channel-forming portion with a length of L2, a width of W2, and a height or a thickness of T2, substantially parallel to the covering portion, the channel-forming portion comprising:
      (i) a first surface and a second surface, the second surface being opposite the first surface at a distance of T2;
      (ii) a first end and a second end, located at each end of the channel-forming portion and the second end opposite the first end at a distance of L2;
      (iii) a microfluidic channel with a length of l, a width of w and a height of h, substantially parallel to the covering portion and formed from the first surface toward the second surface and located between the first and second ends and beneath the covering portion, wherein l<L2<L1, w<W2<W1, and h<T2; and
      (iv) openings, located at the second surface, wherein the openings are in fluidic connections with the microfluidic channel, and
      the channel-forming portion is in contact with the covering portion at the first and the second ends via the first surface;
   (c) a first backing portion and a second backing portion, each having a thickness T3 greater than the channel-forming portion's height T2, located near the first and the second ends of the channel-forming portion and in contact with the second surface thereof; and
   (d) an inlet and an outlet, located near the opposite ends of the microfluidic channel and in fluidic connections with the channel and the openings located at the second surface of the channel forming portion and between the inlet and outlet, the inlet and outlet being formed in the channel-forming portion and the backing portions.

2. The microfluidic hanging drop chip of claim 1, wherein the second surface of the channel-forming portion is substantially flat and/or without protrusion parts thereon.

3. The microfluidic hanging drop chip of claim 1, comprising more than one microfluidic channel.

4. The microfluidic hanging drop chip of claim 1, further comprising a fluid delivery device in a fluidic connection with the inlet and a fluid sucking device in a fluid connection with the outlet.

5. The microfluidic hanging drop chip of claim 1, wherein the covering portion is not adapted to be removable from the channel-forming portion.

6. The microfluidic hanging drop chip of claim 1, further comprising:
   (e) a cell culture medium, located within the microfluidic channel and the openings, wherein the cell culture medium within the openings forms hanging drops.

7. The microfluidic hanging drop chip of claim 6, wherein the hanging drops contain cells.

8. The microfluidic hanging drop chip of claim 1, wherein each opening has a diameter ranging from 1 micrometer to 2500 micrometer.

9. The microfluidic hanging drop chip of claim 1, wherein the channel-forming portion comprises a material selected from the group consisting of polydimethylsiloxane (PDMS), Polyethylene (PE), Polycarbonate (PC), Polystyrene (PS), Polymethyl methacrylate(PMMA), Cyclic Olefin Copolymer (COC), silicon, glass and thermoplastics materials.

10. The microfluidic hanging drop chip of claim 1, wherein the first surface of the channel-forming portion at the first and the second ends thereof is bonded to the covering portion.

11. The microfluidic hanging drop chip of claim 1, which is placed inside a container.

12. The microfluidic hanging drop chip of claim 11, wherein the container further comprises:
   (a) an external inlet in a fluidic connection with the inlet of the chip; and
   (b) an external outlet opposite the external outlet and in a fluidic connection with the outlet of the chip.

13. The microfluidic hanging drop chip of claim 12, wherein the external inlet of the container is in a fluidic connection with a fluid delivery device and the external outlet in a fluidic connection with a fluid sucking device.

14. A method for forming hanging drops, comprising:
   (a) providing the microfluidic hanging drop chip of claim 1;
   (b) causing a fluid to enter and flow through the microfluidic channel via the inlet; and (c) causing formation of hanging drops in the openings, each of the fluidic drops hanging from an opening that contains the fluidic drop.

15. The method acclaim 14, wherein the fluid comprises cells in suspension and the hanging drops comprises the cells.

16. The method of claim 14, wherein each hanging drop has a height H of no greater than the diameter of the opening containing the hanging drop.

17. The method of claim 14, further comprising controlling the height of the hanging drops by changing the hydrostatic pressure of the fluid.

18. The method of 14, further comprising allowing an additional fluid to exit from the outlet.

19. The method of claim 14, wherein the hanging drops do not extend beyond the openings or to the second surface of the channel-forming portion.

20. The method of claim 14, wherein the step of causing the fluid to enter and flow through the microfluidic channel via the inlet is performed under a hydraulic pressure or by a pump.

* * * * *